United States Patent
Fisher et al.

(10) Patent No.: US 8,098,149 B2
(45) Date of Patent: Jan. 17, 2012

(54) WIRELESS PATIENT PARAMETER SENSORS FOR USE IN MRI

(75) Inventors: Stephen Douglas Fisher, Winter Springs, FL (US); Robert A. Harwell, Orlando, FL (US); Joseph F. Lambert, II, Orlando, FL (US); John C. Moore, Broken Arrow, OK (US); Scott Nolan, Oviedo, FL (US); Jorgen Kilden-Pedersen, Orlando, FL (US); Jon Rikenberger, Ormond Beach, FL (US); Arthur R. Weeks, Jr., Oviedo, FL (US); Kenneth Van Arsdel, Orlando, FL (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 613 days.

(21) Appl. No.: 12/440,035

(22) PCT Filed: May 10, 2007

(86) PCT No.: PCT/US2007/068624
§ 371 (c)(1),
(2), (4) Date: Mar. 5, 2009

(87) PCT Pub. No.: WO2007/134143
PCT Pub. Date: Nov. 22, 2007

(65) Prior Publication Data
US 2010/0188208 A1    Jul. 29, 2010

Related U.S. Application Data

(60) Provisional application No. 60/799,884, filed on May 12, 2006.

(51) Int. Cl.
*G08B 1/08* (2006.01)
(52) U.S. Cl. .............. 340/539.12; 340/539.1; 340/573.1
(58) Field of Classification Search ............. 340/539.12, 340/539.1, 573.1
See application file for complete search history.

(56) References Cited

U.S. PATENT DOCUMENTS

| | | | | |
|---|---|---|---|---|
| 6,052,614 A * | 4/2000 | Morris et al. | ................. | 600/509 |
| 2001/0051766 A1 * | 12/2001 | Gazdzinski | ................... | 600/309 |
| 2005/0027191 A1 * | 2/2005 | Uutela et al. | ................... | 600/421 |
| 2005/0107681 A1 | 5/2005 | Griffiths | | |
| 2006/0206024 A1 * | 9/2006 | Weeks et al. | ................... | 600/418 |
| 2006/0241384 A1 * | 10/2006 | Fisher et al. | ................... | 600/414 |
| 2006/0241392 A1 * | 10/2006 | Feinstein et al. | ................ | 600/422 |
| 2006/0247512 A1 * | 11/2006 | Harwell et al. | ............... | 600/410 |
| 2010/0036236 A1 * | 2/2010 | Fisher et al. | .................. | 600/411 |
| 2010/0074365 A1 * | 3/2010 | Ladebeck et al. | ............. | 375/285 |
| 2010/0191069 A1 * | 7/2010 | Fisher et al. | .................. | 600/300 |

* cited by examiner

Primary Examiner — Travis Hunnings

(57) ABSTRACT

A wireless patient monitor for MRI provides for on-board filtering of physiological signals from the patient to provide improved assessment and processing of MRI noise before the signal is affected by the transmission process. A system of powering of a wireless patient monitor using capacitors is also provided.

24 Claims, 3 Drawing Sheets

WIRELESS PATIENT PARAMETER SENSORS FOR USE IN MRI

CROSS-REFERENCE TO RELATED APPLICATIONS

This application claims the benefit of U.S. Provisional Application 60/799,884 filed May 12, 2006 and hereby incorporated by reference.

STATEMENT REGARDING FEDERALLY SPONSORED RESEARCH OR DEVELOPMENT

N/A

BACKGROUND OF THE INVENTION

The present invention relates generally to electronic patient monitors and, in particular, to patient monitors suitable for use in the severe electromagnetic environment of a magnetic resonance imaging machine.

Magnetic resonance imaging (MRI) allows images to be created of soft tissue from faint electrical resonance (NMR) signals emitted by nuclei of the tissue. The resonance signals are generated when the tissue is subjected to a strong magnetic field and excited by a radiofrequency pulse.

The quality of the MRI image is in part dependent on the quality of the magnetic field, which must be strong and extremely homogenous. Ferromagnetic materials are normally excluded from the MRI environment to prevent unwanted magnetic forces on these materials and distortion of the homogenous field by these materials.

A patient undergoing an MRI "scan" may be received into a relatively narrow bore, or cavity, in the MRI magnet. During this time, the patient may be remotely monitored to determine, for example, heartbeat, respiration, temperature, and blood oxygen. A typical remote monitoring system provides "in-bore" sensors on the patient connected by electrical or optical cables to a monitoring unit outside of the bore.

Connecting an in-bore sensor to a monitoring unit may be done with long runs of electrical or optical cables. Such cables can be a problem because they are cumbersome and can interfere with access to the patient and free movement of personnel about the magnet itself.

One solution to these problems of cabling is described in co-pending U.S. patent application Ser. Nos. 11/080,958, filed Mar. 15, 2005, and 11/080,743, filed Mar. 15, 2005, assigned to the assignee of the present invention and hereby incorporated by reference. This patent application describes a wireless patient monitor that may be positioned near the patient to provide real-time monitoring of patient physiological signals during the MRI examination.

The electrical environment of the MRI system produces a considerable amount of electrical noise that may interfere with the collection of physiological signals by in-bore sensors. The noise may include that generated by radio frequency pulses used to stimulate the protons of the patient's tissue into precession and noise induced by rapidly switched gradient magnetic fields. The character of the electrical noise produced by the MRI machine may change depending on the machine and on the particular scan protocols.

In order to reduce the effect of the electrical noise on the acquired physiological signals obtained by in-bore sensors, it is known to provide different types of signal filters, appropriate for different imaging situations, at the monitoring unit outside the bore. An operator observing the physiological signals may select among the different filters to choose a filter that provides a physiological signal with the lowest noise.

When wireless in-bore sensors are used, the transmitted signal must generally be pre-filtered before transmission to limit the bandwidth of the transmitted signal. This pre-filtering is not intended to separate all noise from the physiological signal and generally will not provide the entire optimum filter for this purpose. Nevertheless, to the extent that the pre-filter necessarily modifies the transmitted signal, it limits the ability of the operator to fully assess the amount of noise on the physiological signal and/or to fully control the filtration of the physiological signal.

BRIEF SUMMARY OF THE INVENTION

The present invention provides improved filtration of a wirelessly transmitted physiological signal by providing a set of different electrical and/or firmware pre-filters at the transmitting unit that provide filtering of the physiological signal before or instead of the pre-filtering of the transmitter. In this way, more sophisticated filtration may be performed uncompromised by the pre-filter of the transmitter. The particular signal filter can be selected automatically or by wireless command.

Specifically then, the present invention provides an MRI compatible wireless system for monitoring patient physiological signals including a transmitting unit positionable proximate to the patient during the MRI examination. The transmitting unit includes at least one sensor input for receiving a physiological signal from a sensor communicating with the patient, and a set of electrical and/or firmware filters having different characteristics adapted to provide for signal filtering of MRI electrical interference from the physiological signal. A filter selector within the transmitting unit receives a selection signal during an MRI scan to select one or more of the electrical and/or firmware filters for filtering the physiological signal, and provides this signal to a wireless transmitter which transmits to an external monitoring unit in a manner compatible with the MRI examination.

It is thus one feature of at least one embodiment of the invention that it allows wireless transmission of reduced bandwidth data compatible with filtration optimized for removing MRI-induced noise.

The transmitting unit may include a receiver receiving commands from the external monitor and the selection signal may be a command received from the external monitor.

It is thus another aspect of at least one embodiment of the invention to permit manual selection of a transmitter-based pre-filter.

Alternatively, the transmitting unit may include a noise analyzer monitoring noise in the physiological signal to automatically provide the selection signal.

It is thus another aspect of at least one embodiment of the invention to allow filter selection at the transmitter using an analysis of the unfiltered signal before modification by transmission.

The noise analyzer may monitor the physiological signal as filtered by each of the pre-filters to select the pre-filter providing an output with best characteristics.

It is thus an aspect of at least one embodiment of the invention to provide a simple automatic assessment of signal quality.

The set of electrical and/or firmware pre-filters may be a field programmable gate array and/or a digital signal processor.

It is thus another feature of at least one embodiment of the invention to provide for an extremely compact yet versatile filter implementation.

The set of electrical and/or firmware filters may be tuned to different modes of interference caused by interference from the MRI examination selected from the sources of: magnetic gradient coil interference and radiofrequency coil interference.

It is thus another feature of at least one embodiment of the invention to allow filtration using ex ante knowledge about the MRI process.

The physiological signal is selected from the group consisting of: heart beat, respiration, body temperature, and blood oxygen.

It is an aspect of the present invention that it may provide for different filter types based on the type of physiological signal being transmitted.

The invention also provides a power source for wireless patient monitors using so called "super capacitors", generally capacitors that are one Farad or more in size and thereby avoiding problems of using batteries in the confined and intense magnetic environment of the MRI machine.

More specifically, this aspect of the invention provides a wireless patient sensor for monitoring a patient during an MRI examination having a housing positionable near the patient during the MRI examination and an input circuit for receiving a physiological signal from the patient. The sensor further provides a transmitter for transmitting the physiological signal wirelessly to an external station in a manner compatible with operation of the MRI machine. The sensor is powered by a power source employing capacitor storage without chemical batteries.

It is thus one feature of at least one embodiment of the invention to eliminate the need for costly battery systems that may adversely affect the imaging process through the incorporation of magnetic elements.

The capacitor storage may provide a capacitance of at least one Farad.

It is thus another feature of at least one embodiment of the invention to employ so-called super capacitors as a convenient short-term energy storage system.

The sensor may further include a display displaying a charge on the capacitor storage.

It is thus another feature of at least one embodiment of the invention to provide a simple and accurate assessment of the readiness the sensor.

The display may show one or both of a voltage of the capacitor storage and/or an operating time of the physiological monitor when using the capacitor storage at a given voltage.

It is thus another feature of at least one embodiment of the invention to provide an accurate reading of the charge on the capacitors which may be derived directly from their output voltage.

The sensor may further include a DC-to-DC converter for providing constant voltage output as the capacitor storage voltage drops.

It is thus another aspect of at least one embodiment of the invention to provide a power system that accommodates the steady drop in voltage of a capacitor as power is used.

The DC-to-DC converter may be a boost converter.

It is thus another feature of at least one embodiment of the invention to provide a power system that maximizes the time at which the voltage is at a usable level.

The sensor may be used with a charging station providing receptacles for removable capacitor power sources to receive and charge the removable capacitor power sources when they are held in the receptacles.

It is thus a feature of at least one embodiment of the invention to provide for a simple rapid charging station at the site of use of the portable systems.

The charging station may provide a constant current source for charging the capacitor power sources.

It is another aspect of at least one embodiment of the invention to provide for high-speed charging of the capacitor storage without damage.

The charging station may further include an indicator showing a degree of completion of the charging of each capacitor power source in a receptacle.

It is thus another feature of at least one embodiment of the invention to allow quick determination of the state of charge of the capacitor storage systems prior to use.

The capacitor power sources may be constructed of non-ferromagnetic materials.

It is thus an aspect of at least one embodiment of the invention to provide a power source with improved compatibility with the MRI environment.

These particular features and advantages may apply to only some embodiments falling within the claims and thus do not define the scope of at least one embodiment of the invention.

DETAILED DESCRIPTION OF THE PREFERRED EMBODIMENT

Figure 1:
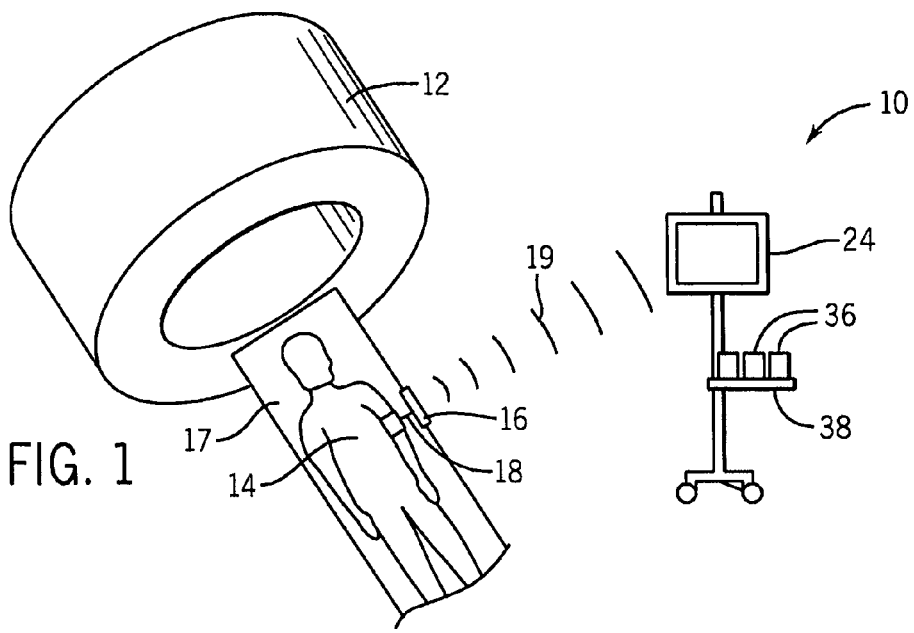
FIG. 1 is a fragmentary perspective view of a magnet of an MRI machine showing a patient positioned before a scan with a patient sensor transmitting patient physiological signals wirelessly to a base unit.

Referring now to FIG. 1, an MRI suite 10 may include an MRI magnet 12 holding various radio frequency and gradient magnetic field coils such as produce substantial electrical interference as is well understood in the art.

A patient 14, supported on a movable table 17, may be positioned outside the bore of the magnet 12 to receive a wireless patient monitor 16 receiving signals from the patient 14 by leads 18. The patient 14 may then be moved into the bore of the magnet 12 with the wireless patient monitor 16 allowing for continuous monitoring of the patient 14. The wireless patient monitor 16 may incorporate its own power supply to transmit the monitored signals from the patient 14 via radio transmitted signal 19 or the like to a base station 24 positioned near the magnet 12 but outside of the bore.

Methods of supporting a wireless transmitter of this kind on a patient are described, for example, in co-pending U.S. patent application 2006/0247512 entitled "Patient Supported In-Bore Monitor For MRI", assigned to the assignee of the present invention and hereby incorporated by reference.

Figure 2:
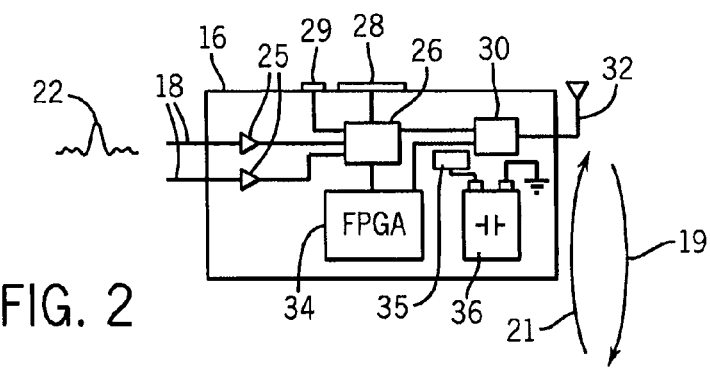
FIG. 2 is a block diagram of the patient sensor and base unit incorporating a field programmable gate array ("FPGA") used to implement multiple digital filters for the present invention.
Figure 3:
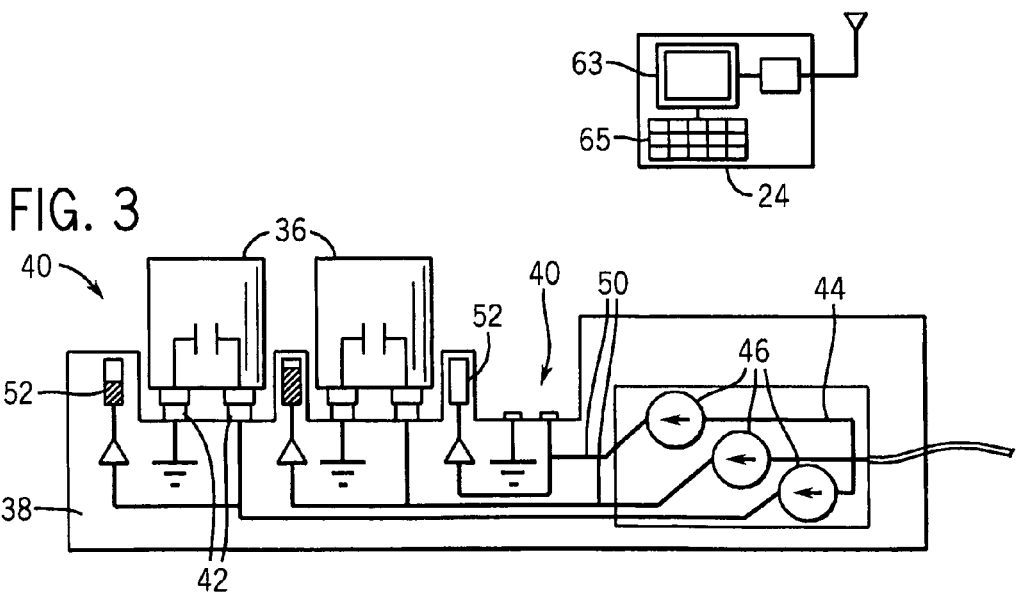
FIG. 3 is a block diagram of a charging stand attached to the base unit and holding supercapacitors for recharging before powering the patient sensor.

Referring now to FIG. 2, the leads 18 of the wireless patient monitor 16 may receive physiological signals 22, for example heartbeat, respiration, body temperature, and blood oxygen, that may be processed by signal conditioning circuitry 25 and provided to a microcontroller 26 to be converted from analog signals to digital signals at a given sampling rate. The microcontroller 26 may communicate with a display 28 to be used in adjusting the patient monitor 16 (for example, at a bedside prior to scanning), verifying its proper operation during commissioning communicating with the base station 24. In this regard, the display 28 may provide for a representation of the received physiological signal 22 or indicator lights indicating the status of the signal. A display system for such a monitor is described in U.S. patent application 2006/0241384 entitled: "Wireless In-Bore Patient Monitor For MRI With Integral Display" assigned to the assignee of the present invention and hereby incorporated by reference.

The display 28 may further be used to associate the wireless patient monitor 16 with a given transmission channel. In this latter regard, the microcontroller 26 may communicate with a transmitter/receiver 30 connected to antenna 32 for transmitting and receiving data with the base station 24 on the channel selected by operating controls 29 to select a transmission channel that is then displayed on the display 28.

Wireless transmission of physiological data in the electrically noisy environment of the MRI suite 10, the noise caused by switched radio frequency and magnetic gradient fields of the MRI machine, without interference by the noise to the transmission and without interference by the transmission to the sensitive receiver electronics of the MRI machine, requires specialized transmission techniques such as those taught in U.S. patent application 2006/0206024 entitled: "Wireless In Bore Patient Monitor For MRI", assigned to the same assignee as the present invention and hereby incorporated by reference.

The microcontroller 26 may also communicate with a field programmable gate array (FPGA) 34 that provides various features of a digital signal processor (DSP) to implement multiple gradient filters used in an automatic gradient filter selection algorithm as will be described further below.

In a preferred embodiment, the circuitry of the signal conditioning circuitry 25, the microcontroller 26, the transmitter/receiver 30, and the FPGA 34 are powered by a supercapacitor 36, being one or multiple discrete capacitors wired together in series or parallel having a capacitance of at least one Farad, contained by the patient monitor 16. In the application of the patient monitor 16, the supercapacitor 36 offers sufficient power density for operating the patient monitor 16 during a normal MRI scan, and avoids ferromagnetic materials or hazardous materials often found in batteries. Ferromagnetic materials can be a problem in the vicinity of the magnet 12 because such materials can be affected by strong forces of attraction of the polarizing magnetic field and/or interfere with the homogeneity of the magnetic field within the magnet bore, homogeneity that is critical to accurate imaging.

Figure 7:
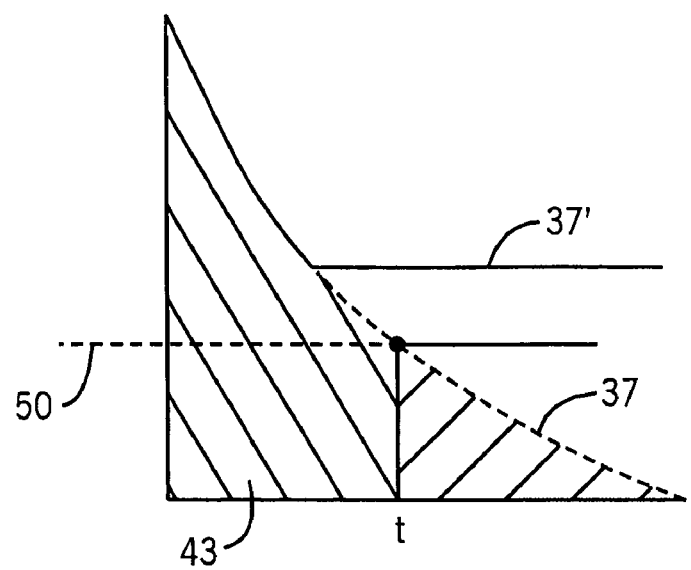
FIG. 7 is a plot of voltage versus time at the capacitor storage and after a boost converter receives the capacitor voltage.

Referring now to FIGS. 2 and 7, during use, the supercapacitor 36 provides an asymptotically declining voltage 37 that may be received by a DC-to-DC converter 35. The DC-to-DC converter may be a so-called "boost" converter that may provide a constant DC voltage 37' even as the voltage 37 drops below that constant level by incorporating a small non-ferromagnetic boost inductor according to techniques well known in the art. In this way, the full energy capacity of the supercapacitor 36 may be utilized despite the decline in capacitor voltage.

Figure 6:
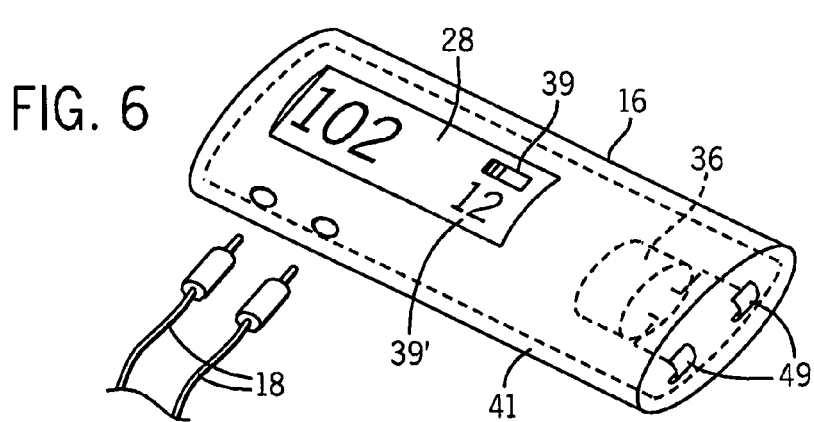
FIG. 6 is a perspective view of the patient unit of FIG. 2 showing two displays of capacitor power reserve in terms of operation time and percent charge.
Figure 8:
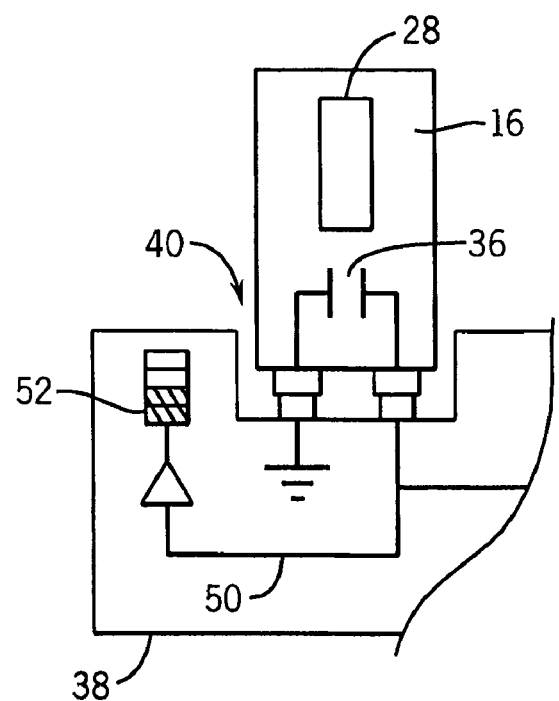
FIG. 8 is a figure similar to that of FIG. 3 showing a charging station accepting the entire patient unit without removal of the capacitor power source.

Referring now to FIGS. 1 and 2, these supercapacitors 36 may be removable from the wireless patient monitor 16 and placed in a charging stand 38 conveniently located on the remote base station 24. Alternatively, and as shown in FIG. 6, the supercapacitors 36 may be wholly incorporated within the RF shielding 41 of the patient monitor 16 with only their terminals 49 exposed and the entire patient monitor 16 may be placed in the charging stand 38 as shown in FIG. 8. In this latter embodiment, provisions for user-access to a battery compartment or the like can be wholly eliminated permitting more robust radiofrequency shielding.

In either case, the charging stand 38 may provide for a series of charging pockets 40 holding either the supercapacitors 36 or the entire patient monitor 16 so that terminals 49 connected to the supercapacitors 36 are exposed to connect to corresponding terminals 42 in the pockets 40. Once placed in the pocket 40, the ground terminal of each supercapacitor 36 may be connected to a ground of a power supply 44 of the charging stand 38, and the positive terminal of each supercapacitor 36 may be connected to an independent current source 46 implemented in the power supply 44. Each current source 46 provides a controlled (and typically constant) current preset to a percentage of the maximum permissible charging current of each supercapacitor 36. The use of the current sources 46 ensure the maximum charging speed of the supercapacitor 36 by changing the charging voltage as necessary to provide a consistent current for charging.

The power supply 44 may also provide voltage signals 50 indicating the voltage on the supercapacitors 36 to indicator gauges 52 each being, in one embodiment, an LED bar gauge showing percentage of total charge on the supercapacitors 36 being a simple function of the voltage on the individual supercapacitors 36. Typically, the supercapacitors 36 will recharge in only a fraction of the time required for comparable batteries and will have a many times higher recharging number than batteries.

Referring again to FIGS. 6 and 7, the wireless patient monitor 16 may also provide displays 39 and 39' providing an indication of the charge on the supercapacitor 36 when installed in a particular wireless patient monitor 16 away from the charging stand 38. Display 39, like indicator gauges 52, may show the percentage of total charge of the supercapacitor 36 such as may be deduced from the voltage signals 50 such as defines a lower area 43 under the curve of asymptotically declining voltage 37 as compared to the total area under the curve of asymptotically declining voltage 37. In addition, the wireless patient monitor 16 may provide for display 39' indicating a remaining running time of the wireless patient monitor 16 deduced simply from the total running time obtained with a fully charged supercapacitor 36 multiplied by the percentage deduced through the analysis of area 43.

Figure 4:
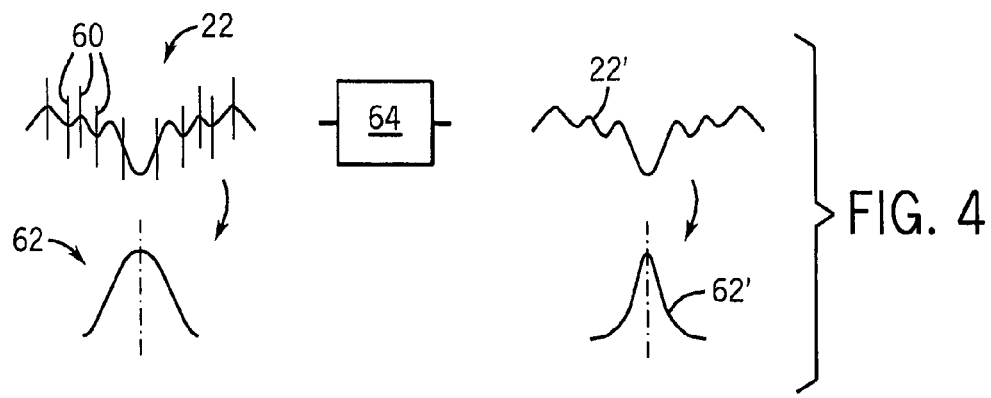
FIG. 4 is a graphical representation of a physiological signal received by the patient sensor of FIG. 1 before and after filtering.

Referring now to FIG. 4, in general, the physiological signals 22 received by the patient monitor 16 will include significant electrical interference 60 caused by induced currents and voltages produced by the coils associated with the MRI magnet 12. The particular type of interference will often be related to the type of imaging being performed, and the degree of interference with the underlying physiological signal 22 may depend on the type of physiological signal 22. The electrical interference 60 will increase the variance 62 of the signal 22 and other statistical measurements, for example, the power spectrum width or the like.

A filter 64, for example, a slew filter, conventional bandpass, lowpass or highpass filter, or other filters well known in the art of digital signal processing, may be applied to physiological signal 22 to produce a clean signal 22' better reflecting the underlying physiological signals 22, with reduced electrical interference 60. Generally, the clean signal 22' will have a smaller variance 62' relative to variance 62 of signal 22.

Figure 5:
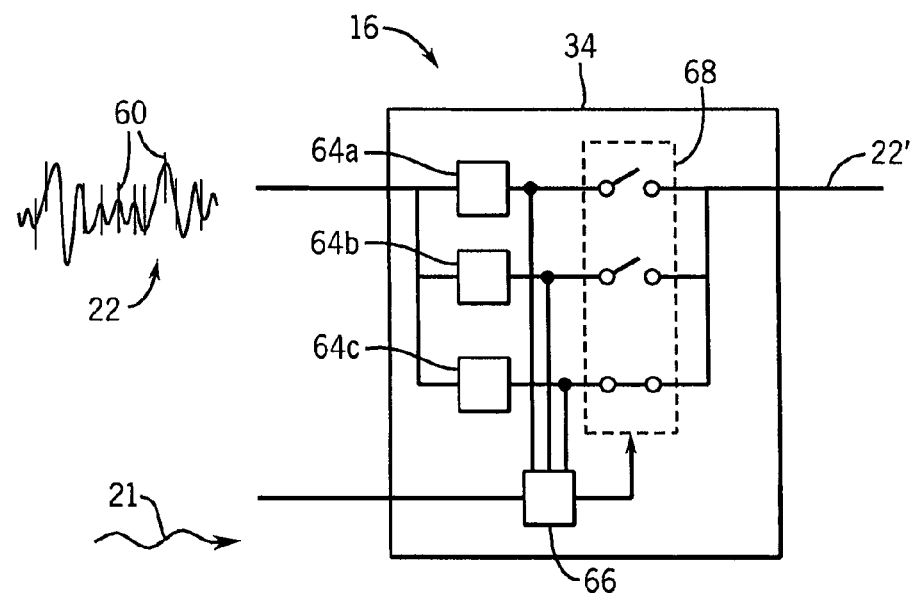
FIG. 5 is a block diagram of a set of filters implemented by the FPGA of FIG. 2 showing implementation of multiple filters in parallel and the selection of individual filters by a selector receiving a selection signal either remotely or locally through an analysis of variance or other statistical measure of the physiological signals.

Referring to FIG. 5, the FPGA 34 may accordingly implement multiple filters 64a, 64b and 64c (or more) having filter parameters selected to be appropriate for particular MRI machines or imaging sequences or physiological signals 22. Each of the filters 64a, 64b, and 64c may operate in parallel on the signal 22 and electrical interference 60. The outputs of each filter 64a, 64b, and 64c are provided to a variance analyzer 66 to determine the filter 64a, 64b, and 64c that appears to best be reducing the electrical interference 60, for example, by lowest statistical variance. Other techniques of estimating noise reduction may alternatively be used.

The variance analyzer 66 automatically selects through a switch array 68, implemented in software, one filter 64a, 64b and 64c providing the best filtration without the need for operation intervention. Alternatively, and referring to FIGS. 2 and 5, the switch array 68 may be manually controlled by a control signal communicated wirelessly from the base station 24 via a transmitted signal 21. In this case, the particular filter is selected by the operator viewing the transmitted physiological signal 22 (as filtered by the different filters 64a, 64b, or 64c) entering a desired filter or filter parameter on keyboard or entry panel 65. No pre-filtering of the transmitted signal 19 is required other than the selection of one of the selectable filters 64a, 64b, or 64c. Because one filter will be selected by default, in one embodiment, no separate bandwidth reducing filter is needed to provide for bandwidth reduction prior to wireless transmission. Or, in the case where a separate bandwidth reducing filter is retained, the analysis of the variance, for example, can occur before this bandwidth reduction providing filter. In either case, only the filtered signal 22' needs to be transmitted; thus, significantly reducing the burden and bandwidth of the wireless transmission.

It is specifically intended that the present invention not be limited to the embodiments and illustrations contained herein and the claims should be understood to include modified forms of those embodiments including portions of the embodiments and combinations of elements of different embodiments as come within the scope of the following claims.

We claim:

1. An MRI compatible wireless patient monitoring system which is positionable proximate to the patient during the MRI examination and comprising:
    at least one sensor input for receiving a physiological signal from a sensor communicating with the patient;
    a set of signal filters having different characteristics adapted to provide for electrical filtering of MRI-induced electrical interference from the physiological signal;
    a filter selector receiving a selection signal during an MRI scan to select one of the electrical filters for filtering the physiological signal; and
    a wireless transmitter receiving the physiological signal as filtered by the selected electrical filter and transmitting the physiological signal wirelessly to an external monitoring unit in a manner compatible with the MRI examination.

2. The patient monitoring system of claim 1 further including a receiver receiving commands from the external monitor transmitted wirelessly to the receiver in a manner compatible with the MRI examination, and wherein the selection signal is a command received from the external monitor.

3. The patient monitoring system of claim 1 further including a noise analyzer monitoring noise in the physiological signal to automatically provide the selection signal.

4. The patient monitoring system of claim 1 wherein the noise analyzer monitors the physiological signal as filtered by each of the filters to select the filter providing an output with a lowest variance.

5. The patient monitoring system of claim 1 wherein the set of electrical filters are implemented by a field programmable gate array.

6. The patient monitoring system of claim 1 wherein the set of electrical filters are implemented by a digital signal processor.

7. The patient monitoring system of claim 1 wherein the set of electrical filters are tuned to different modes of interference caused by interference from the MRI examination selected from the sources of: magnetic gradient coil interference and radiofrequency coil interference.

8. The patient monitoring system of claim 1 wherein in the physiological signal is selected from the group consisting of: heart beat, respiration, body temperature, and blood oxygen.

9. A method of monitoring of patient physiological signals during an MRI examination comprising: (a) positioning a transmitting unit proximate to the patient during the MRI examination to receive a physiological signal from a sensor communicating with the patient; (b) selecting among a set of electrical filters in the transmitting unit having different characteristics adapted to provide for electrical filtering of MRI induced interference from the physiological signal; and (c) transmitting the physiological signal as filtered by the selected filter wirelessly to an external monitoring unit in a manner compatible with the MRI examination.

10. The method of claim 9 wherein the transmitting unit further receives commands from the external monitor transmitted wirelessly to the transmitting unit in a manner compatible with the MRI examination to select among the filters.

11. The method of claim 9 further including the step of analyzing noise in the physiological signal at the transmitting unit to automatically select the filter.

12. The method of claim 10 wherein the filter providing an output with best statistical characteristics is selected.

13. The method of claim 9 wherein the electrical filters are tuned to different modes of interference caused by interference from the MRI examination selected from the sources of: magnetic gradient coil interference and radiofrequency coil interference.

14. The method of claim 9 wherein in the physiological signal is selected from the group consisting of: heart beat, respiration, body temperature, and blood oxygen.

15. The patient monitoring system of claim 1, further including:
    a power source providing power for the sensor input and the wireless transmitter, the power source comprising a capacitor storage without chemical batteries.

16. The patient monitoring system of claim 15 wherein the capacitor storage provides a capacitance of at least one Farad.

17. The patient monitoring system of claim 15 further including a display displaying a charge on the capacitor storage.

18. The patient monitoring system of claim 17 where the display displays one of a voltage of the capacitor storage and an operating time of the physiological monitor when using the capacitor storage at a given voltage.

19. The patient monitoring system of claim 15 further including a DC-to-DC converter for providing constant voltage output as the capacitor storage voltage drops.

20. The patient monitoring system of claim 19 where in the DC-to-DC converter is a boost converter.

21. The patient monitoring system of claim 15, wherein the capacitor storage includes a removable capacitor power source; and further including:

a charging station providing receptacles for removable capacitor power sources to receive and charge the removable capacitor power sources when they are held in the receptacles.

22. The patient monitoring system of claim 21 wherein the charging station provides a constant current source for charging the capacitor power sources.

23. The patient monitoring system of claim 21 wherein the charging station further includes an indicator showing a degree of completion of the charging of each capacitor power source in a receptacle.

24. The patient monitoring system of claim 21 wherein the capacitor power sources are constructed of non-ferromagnetic materials.

* * * * *